United States Patent [19]
Komagata et al.

[11] Patent Number: 5,804,186
[45] Date of Patent: Sep. 8, 1998

[54] NERVE CELL DIFFERENTIATION PROMOTER

[75] Inventors: Daisuke Komagata, Tokyo; Tomio Morino, Oumiya, both of Japan

[73] Assignee: Nippon Kayaku Kabushiki Kaisha, Tokyo, Japan

[21] Appl. No.: 737,242

[22] PCT Filed: May 15, 1995

[86] PCT No.: PCT/JP95/00925

§ 371 Date: Nov. 13, 1996

§ 102(e) Date: Nov. 13, 1996

[87] PCT Pub. No.: WO95/31992

PCT Pub. Date: Nov. 30, 1995

[30] Foreign Application Priority Data

May 23, 1994 [JP] Japan ................................... 6-130796

[51] Int. Cl.⁶ .................................................. A61K 35/74

[52] U.S. Cl. .................. 424/117; 435/70.2; 435/70.4; 435/170; 435/253.5; 435/884

[58] Field of Search ........................ 424/117; 435/70.2, 435/70.4, 170, 253.5, 886

[56] References Cited

FOREIGN PATENT DOCUMENTS

94/05679  3/1994  WIPO .

*Primary Examiner*—Jean C. Witz
*Attorney, Agent, or Firm*—Nields, Lemack & Dingman

[57] ABSTRACT

A nerve cell differentiation promoter which comprises a physiologically active substance NK175203 or a pharmacologically acceptable salt thereof as an active ingredient is provided. It is expected that the nerve cell differentiation promoter of the present invention is applicable to a medicine for dementia, a nerve cell protective medicine or a medicine for peripheral neuropathy caused by anticancer agents.

2 Claims, 2 Drawing Sheets

*; P<0.05

**; P<0.01

NERVE CELL DIFFERENTIATION PROMOTER

TECHNICAL FIELD

The present invention relates to a novel nerve cell differentiation promoter which comprises a physiologically active substance NK175203 or a pharmacologically acceptable salt thereof as an active ingredient and which is expected to be usable as, for example, a medicine for dementia, a nerve cell protective medicine or a medicine for peripheral neuropathy.

BACKGROUND ART

The physiologically active substance NK175203 is a publicly known compound described in International Patent Publication No. WO94/05679.

It is reported that this compound has an activity as a bone marrow cell proliferation promoter.

It has been proved in vitro that a nerve growth factor (hereinafter referred to as NGF) elongates neurites, regulates the production of a neurotransmitter and exerts an effect on the regeneration of the nerve cells of an aged animal [Age, 8, 19 (1985)]. On the other hand, it is known that when NGF is added to an established cell line PC12 which has been cloned from a rat pheochromocytoma, the PC12 cell ceases the proliferation and differentiates into adrenergic neuron cells having neurites. Because of these effects, NGF has recently attracted attention as one of medicines for dementia. By using these cells, it has been clarified that a fibroblast growth factor and interleukin 6 induce the elongation of neurites similarly to NGF. Recently, it has been reported that staurosporine, which is a low molecular weight substance derived from a microorganism, also induces the elongation of neurites [Shinkei Kagaku, 26, 200–220 (1987)].

The staurosporine as described above is highly valuable in medical treatments, since it is a low molecular weight substance, different from NGF. However, it is regrettably considered that there is room for further investigation in the practical application of the same due to its high toxicity.

Under these circumstances, it is highly important in medical treatments to provide a low molecular weight substance which has a lower toxicity and exhibits the effect of elongating neurites at a low concentration.

DISCLOSURE OF INVENTION

As the results of extensive studies, the present inventors have found out that a physiologically active substance NK175203 or a pharmacologically acceptable salt thereof has an activity for promoting the differentiation of nerve cells.

The present invention has thus been completed on the basis of this finding.

Accordingly, the present invention relates to a nerve cell differentiation promoter which comprises the physiologically active substance NK175203 or a pharmacologically acceptable salt thereof as an active ingredient together with pharmaceutically acceptable excipient(s) or carrier(s). The present invention further relates to a medicine for dementia, a nerve cell protective medicine and a medicine for peripheral neuropathy comprising the physiologically active substance NK175203 or a pharmacologically acceptable salt thereof as an active ingredient together with pharmaceutically acceptable excipient(s) or carrier(s).

BRIEF DESCRIPTION OF DRAWING

FIG. 2 shows the effect of NK175203 on improving the sensory nerve function (heat sensitivity) depressed by the administration of Adriamycin (ADM). FIG. 2a shows the test result on the 72nd day from the initiation of the experiment, while

BEST MODE FOR CARRYING OUT THE INVENTION

Figure 1:
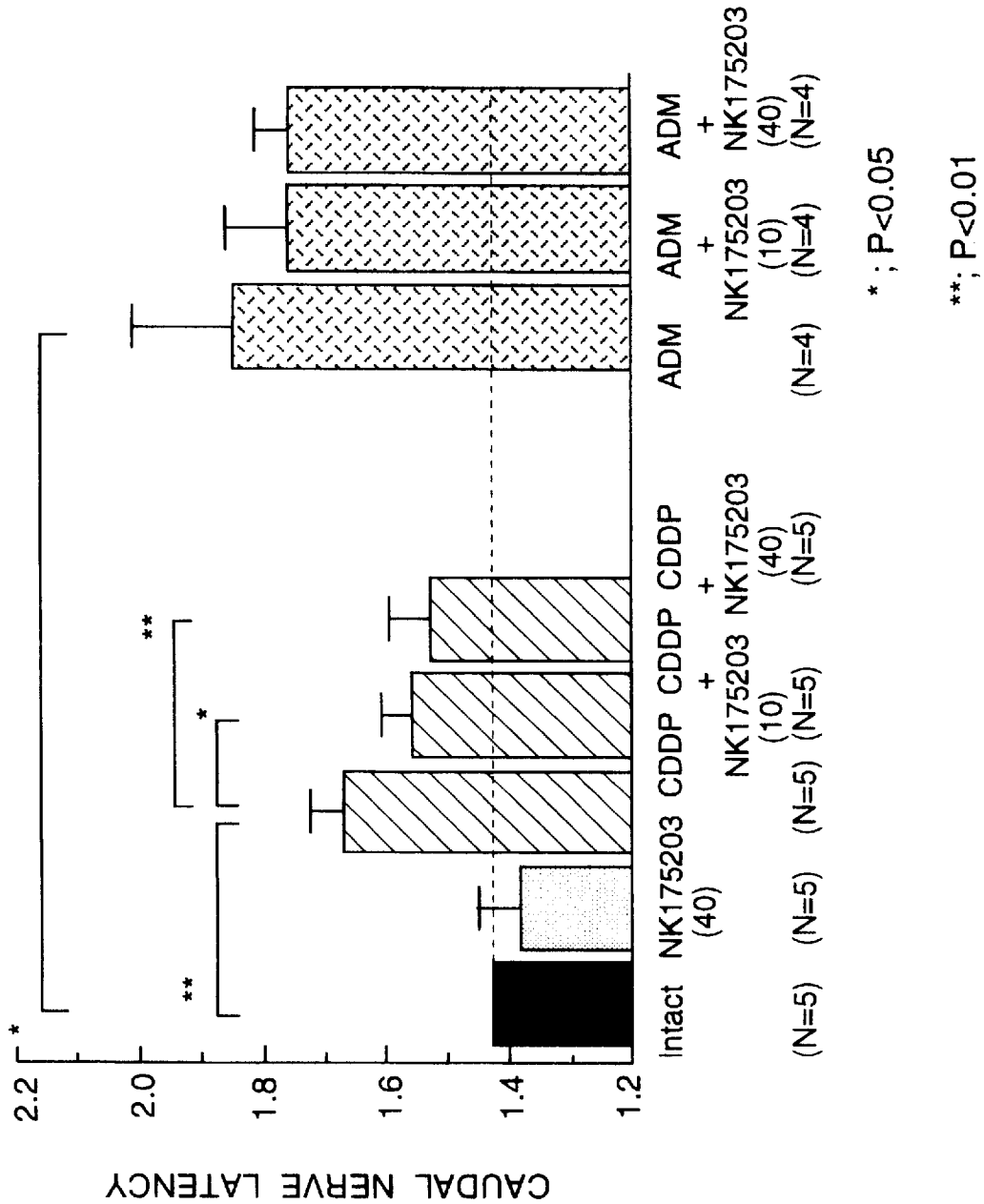
FIG. 1 shows the effect of NK175203 on improving the caudal nerve latency increased by the administration of an anticancer agent.

The physiologically active substance NK175203 to be used in the present invention can be produced and obtained in accordance with the method described in International Patent Publication No. WO94/05679.

More specifically, it can be obtained by culturing a microorganism belonging to a genus Streptomyces and producing the above-mentioned physiologically active substance NK175203 (for example, FERM BP-4372) in a medium, accumulating the physiologically active substance NK175203 in the culture and then collecting the same.

The physiologically active substance NK175203 which is the compound used in the present invention may be in the form of a pharmacologically acceptable salt thereof. Examples of such a salt include salts with alkali metals such as sodium and potassium and salts with alkaline earth metals such as calcium.

The nerve cell differentiation promoter of the present invention comprising the physiologically active substance NK175203 as an active ingredient promotes the differentiation of nerve cells, and is therefore effective for repairing and treating various damages to nerve cells. Thus the promoter is expected to be usable as, for example, a medicine for dementia, a medicine for peripheral neuropathy caused by anticancer agents, diabetes, etc., or a nerve cell protective medicine.

When the compound of the present invention is to be used as a nerve cell differentiation promoter, it is administered in the form of injections, oral preparations, suppositories, etc., either alone or as a mixture thereof with excipient(s) or carrier(s). As the excipients and carriers, selection is made of pharmaceutically acceptable ones, and the type and composition thereof are determined depending on the administration route and administration manner. As a liquid carrier, for example, used may be water, alcohols, animal and vegetable oils such as soybean oil, peanut oil, sesame oil and mineral oil, and synthetic oils. As a solid carrier, used may be, for example, sugars such as maltose and sucrose, amino acids, cellulose derivatives such as hydroxypropylcellulose, and organic acid salts such as magnesium stearate.

In the case of an injection, it is generally desirable to use physiological saline, various buffers, solutions of sugars such as glucose, inositol and mannitol or glycols such as ethylene glycol, propylene glycol and polyethylene glycol. It may be also possible that the compound of the present invention is dissolved, prior to the administration, in an appropriate solvent for injection (for example, a liquid for intravenous administration such as sterilized water, physiological saline, a glucose solution, an electrolyte solution or an amino acid solution) together with an excipient such as a sugar, for example, inositol, mannitol, glucose, mannose, maltose or sucrose, or an amino acid, for example, phenylalanine.

The content of this compound in the formulation is usually in the range from 0.1 to 100% by weight, preferably from 1 to 98% by weight, though it widely varies from formulation to formulation. In the case of an injection, for example, the content of the active ingredient is usually in the range from 0.1 to 30% by weight, preferably from 1 to 10% by weight. When orally administered, the compound is formulated together with the above-mentioned solid or liquid carrier(s) into tablets, capsules, powders, granules, solutions, dry syrups, etc. The capsules, tablets, granules and powders generally contain from 5 to 100% by weight, preferably from 25 to 98% by weight, of the active ingredient.

The dose may be determined depending on the age, body weight and conditions of the patient, the purpose of the treatment, etc. The therapeutic dose is generally in the range of from 1 to 100 mg/kg·day when parenterally administered, and from 5 to 500 mg/kg·day when orally administered.

The compounds of the present invention are characterized by having a low toxicity and showing only a small accumulated toxicity when continuously administered. When intraperitoneally administered at once to a mouse in a dose of 500 mg/kg, the compound of the present invention shows no symptom of toxicity.

To further illustrate the present invention in greater detail, the following Examples will be given. However, it is to be understood that the present invention is not restricted thereto so long as it does not depart from the spirit and scope of the same.

EXAMPLE 1

Test of neurite elongation of PC12 cells by physiologically active substance NK175203

The results were judged on the basis of morphological changes in accordance with the method of Green et al., Ann. Rev. Neurosi., 3, 353 (1980).

More specifically, PC12 cells were inoculated into Dulbecco's modified Eagle medium containing 10% of fetal bovine serum and 10% of horse serum in such a manner as to give a cell density of $1\times10^4$/ml and then incubated overnight in a collagen-coated 96-well multiplate at 37° C. under 5% of $CO_2$. Next, a sample was added thereto and the morphological changes were microscopically observed after one day.

As a result, the effective concentration of the physiologically active substance NK175203 on inducing the neurite elongation of the PC12 cells widely varied from 20 to 2.0 μg/ml.

In the above method, the PC12 cells were exterminated after one day due to the cytotoxicity of the physiologically active substance NK175203 at a concentration of 50 μg/ml. This concentration is 2.5 to 25 times higher than the effective concentration of the substance for promoting the nerve cell differentiation, which means that the physiologically active substance NK175203 has a relatively low toxicity.

EXAMPLE 2

Test of Physiologically active substance NK175203 on anticancer agent-induced peripheral neuropathy model Examination was made on the effect of the physiologically active substance NK175203 on improving an anticancer agent-induced peripheral neuropathy model. Male CDF1 mice aged 5 weeks were employed as the test animals. The neuropathy was induced by cisplatin (hereinafter referred to simply as CDDP) or Adriamycin (hereinafter referred to simply as ADM). CDDP was intraperitoneally administered in a dose of 5 mg/kg on the 0th, 7th, 14th, 21st, 28th and 32nd days from the initiation of the experiment, while ADM was administered via the tail vein in a dose of 10 mg/kg on the 0th, 4th and 14th days from the initiation of the experiment. As a medicine for examining the improving effect, NK175203 was used. NK175203 was administered thrice a week (Monday, Wednesday and Friday) for 6 weeks. The day of the initiation of the experiment (i.e., the 0th day) was Monday. The drugs were each dissolved in physiological saline before using. Table 1 summarizes the dose and administration route of each group. The caudal nerve latency was measured on the 0th to 42nd days from the initiation of the experiment. A tail-flick test (a heat sensitivity examination) was carried out on the 72nd and 85th days.

TABLE 1

CDDP- or ADM-induced peripheral neuropathy model groups

| Group | Neuropathy-induction | Medicine administered and dose thereof | Number of animals |
|---|---|---|---|
| 1 | none | none | 6 |
| 2 | none | NK175203 40 mg/kg (intraperitoneally), thrice/week × 6 weeks | 5 |
| 3 | CDDP | none | 5 |
| 4 | CDDP | NK175203 10 mg/kg (intraperitoneally), thrice/week × 6 weeks | 5 |
| 5 | CDDP | NK175203 40 mg/kg (intraperitoneally), thrice/week × 6 weeks | 5 |
| 6 | ADM | none | 5 |
| 7 | ADM | NK175203 10 mg/kg (intraperitoneally), thrice/week × 6 weeks | 5 |
| 8 | ADM | NK175203 40 mg/kg (intraperitoneally), thrice/week × 6 weeks | 5 |

(i) Measurement of caudal nerve latency

The caudal nerve latency was measured in the following manner. A mouse was lightly etherized and fixed face upward onto a cork plate. As a recording electrode, a concentric electrode was penetrated into the tail on the peripheral side at a distance of 2 cm from the base. Further, two needle electrodes were inserted into a site 4 cm apart therefrom as stimulating electrodes. The stimulation was input from the stimulating electrode for a persistence time of 0.05 msec at 5 to 10 V via a stimulation device (Model SEN-7203, mfd. by Nippon Kohden Corporation) and an isolator (Model SS-320J, mfd. by Nippon Kohden Corporation). The action potentials, which were obtained via the recording electrodes and an amplifier (Model EI-601G, mfd. by Nippon Kohden Corporation), of 20 to 50 stimulations were added up. Then the average was calculated and recorded with an X-Y recorder (Model WX-2400, mfd. by Graphtec Corp.). The latent time of the action potential thus obtained was divided by the distance between the stimulated site and the recording site to thereby give the conduction velocity.

On the 42nd day from the initiation of the experiment, the caudal nerve latency was measured. FIG. 1 shows the results. Compared with the intact group, the group of the administration of CDDP alone showed a significantly reduced conduction velocity, which indicated that neuropathy had been induced. On the other hand, the groups of the combined use of CDDP with NK175203 showed each a significantly increased conduction velocity compared with the group of the administration of CDDP alone. When the decrease of the velocity due to the administration of CDDP is taken as 100%, the groups of the combined use of CDDP with 10 and 40 mg/kg of NK175203 showed the improving effects of 45 and 60% respectively in a dose dependent manner.

(ii) Tail-flick test (heat sensitivity examination)

The tail-flick test was carried out in the following manner. A thermal lamp of a Natsume Thermal Counter (mfd. by Natsume) irradiated at 6 V. After preliminarily heating the measuring board by irradiating with the lamp for 30 seconds, the lamp was switched off. Then a mouse set in a circular cylinder for fixation was quickly placed under the lamp. Then the tail of the mouse was irradiated with the thermal lamp about 10 cm above and the time required until the mouse sensed heat and flicked its tail was measured.

Figure 2A:
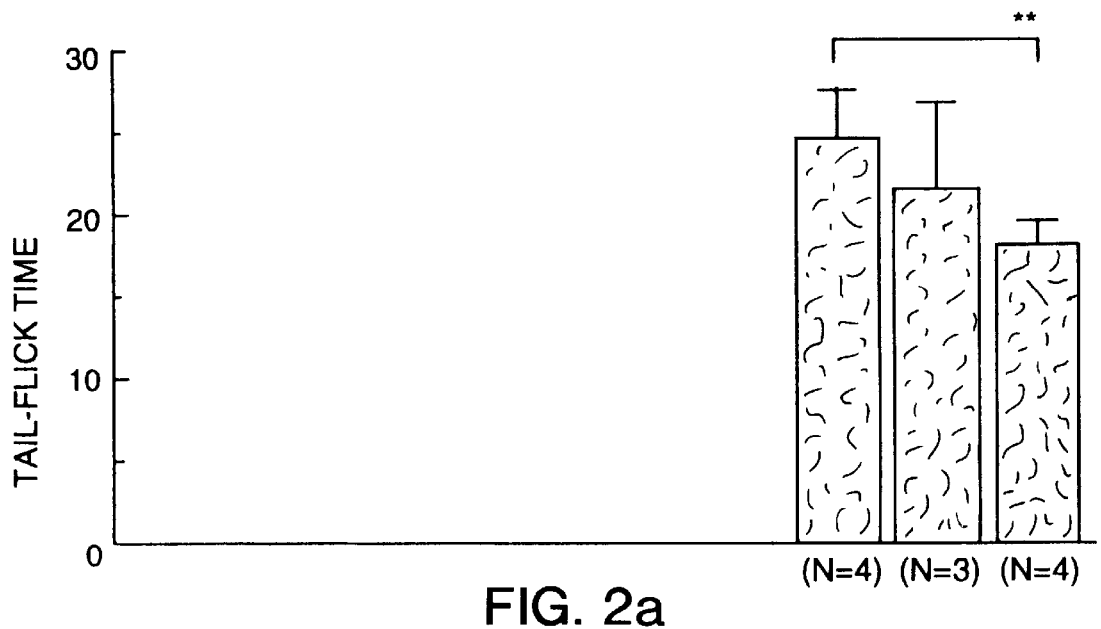

On the 72nd day from the initiation of the experiment, the groups of ADM-induction models were subjected to the first tail-flick test. The site 4 cm apart from the tail base was irradiated with the thermal lamp. FIG. 2a shows the results. Compared with the group of the administration of ADM alone, the group with the combined use of ADM with 40 mg/kg of NK175203 showed a significantly shortened flick time, thus indicating an improvement in the response to the heat stimulation.

Figure 2B:
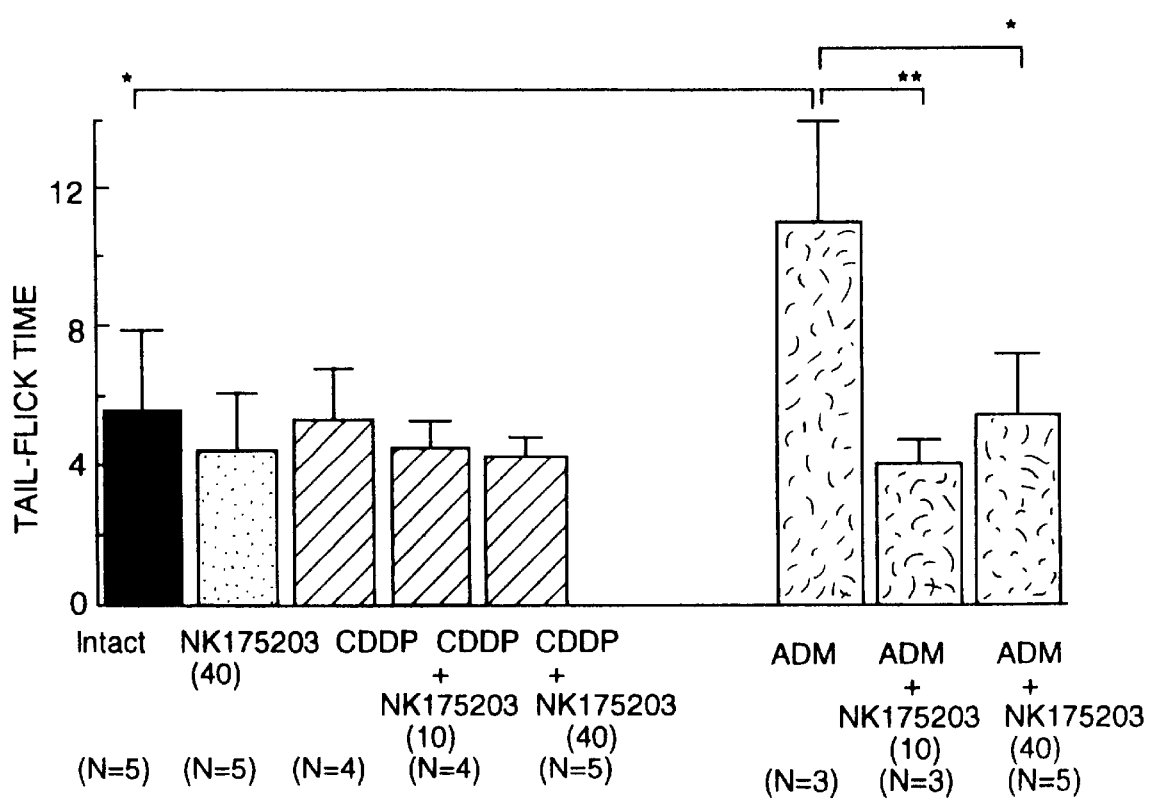
FIG. 2b shows the test result on the 85th day from the initiation of the experiment.

Next, the second test was conducted on the 85th day. The site 3 cm apart from the tail base was irradiated with the thermal lamp. FIG. 2b shows the results. Compared with the intact group, the group with the administration of ADM showed a significantly delayed flick time, thus indicating that the response to the heat stimulation had been depressed by the administration of ADM. Further, the groups with the combined use of ADM with NK175203 showed flick times similar to that of the intact group, thus indicating that the sensory nerve function depressed by the administration of ADM had been clearly ameliorated.

Based on these results, it has been confirmed that NK175203 exerts an improving effect on the mouse anticancer agent-induced peripheral neuropathy models.

EXAMPLE 3 (Formulation Example 1)

Production of granules:

Fifty parts by weight of sodium salt of the physiologically active substance NK175203, 600 parts by weight of lactose, 330 parts by weight of crystalline cellulose and 20 parts by weight of hydroxypropyl-cellulose were well mixed together. Then the obtained mixture was compressed by using a roll compressor (Roller Compactor™), ground and dressed through 16-mesh and 19-mesh sieves to thereby give granules.

EXAMPLE 4 (Formulation Example 2)

Production of tablets:

One hundred parts by weight of sodium salt of the physiologically active substance NK175203, 90 parts by weight of crystalline lactose, 107 parts by weight of crystalline cellulose and 3 parts by weight of magnesium stearate were mixed in a V-type mixer and then the obtained mixture was shaped into tablets each weighing 300 mg.

EXAMPLE 5 (Formulation Example 3)

Production of injection:

To 50 parts by weight of sodium salt of the physiologically active substance NK175203 and 120 parts by weight of mannitol was added distilled water so as to give a total volume of 2,000 parts. After dissolution, the solution was sterilely filtered through a millipore filter of GS type. The filtrate was introduced in 2-g portions into 10 ml vials and freeze-dried to thereby give a freeze-dried powder for injection containing 50 mg/vial of the sodium salt of the compound of the present invention.

INDUSTRIAL APPLICABILITY

As described above, the physiologically active substance NK175203 or a pharmacologically acceptable salt thereof has an activity for accelerating the elongation of neurites of PC12 cells and a relatively low toxicity. Thus it is useful as a nerve cell differentiation promoter and expected to be applicable to, for example, a medicine for dementia, a medicine for peripheral neuropathy caused by anticancer agents, diabetes, etc., or a nerve cell protective medicine.

We claim:

1. A method for promoting nerve cell differentiation comprising administering an effective amount of the substance NK175203 or a pharmacologically acceptable salt thereof together with a pharmaceutically acceptable excipient or carrier to an individual in need thereof.

2. A method for treating peripheral neuropathy comprising administering an effective amount of the substance NK175203 or a pharmacologically acceptable salt thereof together with a pharmaceutically acceptable excipient or carrier to an individual in need thereof.

* * * * *